United States Patent

Farin

[11] Patent Number: 6,063,084
[45] Date of Patent: May 16, 2000

[54] DEVICE FOR HF-COAGULATION OF BIOLOGICAL TISSUES BY MEANS OF FLEXIBLE ENDOSCOPY

[75] Inventor: Günter Farin, Tübingen, Germany

[73] Assignee: Erbe Elektromedizin GmbH, Germany

[21] Appl. No.: 09/122,045

[22] Filed: Jul. 24, 1998

[30] Foreign Application Priority Data

Jul. 24, 1997 [DE] Germany .............. 197 31 931

[51] Int. Cl.⁷ .................................. A61B 17/39
[52] U.S. Cl. ...................... 606/49; 606/40; 606/41
[58] Field of Search .................. 606/27–31, 40–42, 606/45–50

[56] References Cited

U.S. PATENT DOCUMENTS

| | | |
|---|---|---|
| 5,098,430 | 3/1992 | Fleenor . |
| 5,122,138 | 6/1992 | Manwaring ............... 606/46 |
| 5,207,675 | 5/1993 | Canady ..................... 606/40 |
| 5,472,442 | 12/1995 | Klicek ...................... 606/42 |
| 5,540,683 | 7/1996 | Ichikawa et al. .......... 606/40 |
| 5,669,907 | 9/1997 | Platt, Jr. et al. ........... 606/48 |
| 5,693,044 | 12/1997 | Cosmescu ................ 606/42 |
| 5,720,745 | 2/1998 | Farin et al. ............... 606/49 |

FOREIGN PATENT DOCUMENTS 41 39 029 C2  5/1996  Germany .

*Primary Examiner*—Michael Peffley
*Attorney, Agent, or Firm*—St. Onge Steward Johnston & Reens LLC

[57] ABSTRACT

The invention relates to a device for HF-coagulation of biological tissues by means of flexible endoscopy. The invention includes a mobile applicator in a working channel of the endoscope catheter for supplying ionizable gas and containing a current supply connection line to an active mobile electrode at the distal end. According to the invention, the active electrode, relative to the distal end of the endoscope catheter, is movable into the said distal end for non-contact coagulation and out of it for contact coagulation. The respective position of the active electrode or electrode point is monitored by a sensor and, on the basis of a sensor signal upon reaching the retracted position of the electrode, a release takes place for igniting a plasma discharge.

16 Claims, 1 Drawing Sheet

DEVICE FOR HF-COAGULATION OF BIOLOGICAL TISSUES BY MEANS OF FLEXIBLE ENDOSCOPY

BACKGROUND OF THE INVENTION

The invention relates to a device for HF-coagulation of biological tissues by means of flexible endoscopy, a mobile applicator for supplying ionizable gas and containing a current supply connection line to an active mobile electrode able to be placed in a working channel of the endoscope catheter at the distal end.

A device for coagulating of biological tissues, particularly in the gastrointestinal tract, is known from Patent DE 41 39 029 C2. A connecting line for connection to an HF voltage source is located in a working channel of an endoscope. In addition, an ionizable gas is supplied through the working channel, which emerges at the distal end of the working channel. Provided in the flow path of the gas in front of the outlet from the outlet opening is an electrode, which serves to ionize the gas and to supply the coagulation current. The electrode is fixed in position in such a way that it cannot come into contact with the tissue to be coagulated. Undesirable burning or other irreversible damage to the tissue is, therefore, to a large degree eliminated in the solution indicated above.

There is known from U.S. Pat. No. 5,207,675 a coagulation device which likewise can be used in conjunction with an endoscope. Within a flexible tube, which is accommodated by the catheter of the endoscope, there is located a current supply, which is in turn connected to an electrode provided at the distal end. The electrode merges into an electrode point, in order to permit a controlled arc discharge.

Patent WO 93/01758 discloses a pipeline which serves to supply an ionizable gas such as argon, and in the distal end of which an electrode is movably arranged in such a way that it can be advanced from a position within the pipeline to a position partly or wholly outside the distal end of the pipeline.

Both in exogenic methods for blood stypsis by means of hot probes and also in endogenic methods by means of HF-current, the source of bleeding must be brought into thermal or electrically conductive contact with the probe or the coagulation electrode. Problems, however, exist in that the coagulate can adhere securely to the probe or the coagulation electrode, so that when the electrode is removed the source of bleeding is again torn open. Finally, the known methods for stypsis of large area diffuse sites of bleeding are extremely time-consuming. In the known argon-plasma coagulation, there is no direct contact between the active electrode and the tissue surface to be treated. Rather the voltage present at the electrode ignites a plasma discharge of the supplied ionizable gas, namely argon. The advantage of argon-plasma coagulation resides on the fact that the depth and the effective thickness of the coagulation is limited by a developing, thin, 2nd electrically insulating layer on the tissue layer treated. Not least for this reason, argon-plasma coagulation plays an important part in applications in the gastrointestinal tract.

It is, however, disadvantageous that HF surgical instruments, which have previously become known particularly for flexible endoscopy, are not simply suited for contact coagulation or for non-contact coagulation and/or for cutting. Due to the different currents and voltages which are necessary for the respective treatment method, there is a risk that when the active electrode is brought into contact with the tissue, during deliberate non-contact mode, irreversible tissue alterations will occur.

Hence, there is a need for an apparatus to provide HF coagulation of biological tissues without altering the tissues or tearing the tissues upon removing the apparatus. It is further desired to provide a HF coagulation apparatus that can be used in conjunction with an endoscope and catheter and permits both contact and non-contact coagulation.

SUMMARY OF THE INVENTION

It is therefore the object of the invention to indicate an arrangement for HF-coagulation of biological tissues by means of flexible endoscopy, which permits both operation in the range of contact coagulation and also for non-contact coagulation and/or cutting, ensuring that undesirable injuries or alterations in the tissue present are avoided.

The basic idea of the invention resides in the fact that a sensor is provided, preferably in the region of the distal end, which monitors whether the active electrode of the instrument in the distal area is located inside or outside the endoscope catheter. By means of the sensor, it is ensured that the non-contact mode can only be actuated if the active electrode or its distal end is located within the endoscope catheter.

Accordingly, therefore, the active electrode, relative to the distal end of the endoscope catheter, is movable into said distal end for non-contact coagulation and movable out of it for contact coagulation. The position of the active electrode is monitored by the abovementioned sensor. Further, the plasma discharge is ignited only upon a sensor signal given when the electrode has reached the retracted position.

According to the invention, it is possible that the sensor or the sensor output signal is in contact with a current supply unit for generating HF-current and voltage, depending on the indirectly detected position of the active electrode, optimal values can be automatically selected from a predetermined current potential range for the respective treatment method.

In a preferred embodiment, the sensor is a spring-loaded micro-switch contact which is located at the distal end of the applicator. Alternatively, the sensor can be a miniature light barrier located at the distal end of the applicator or in said end. It is likewise possible to design the sensor as a plate condenser, an alteration in the dielectric properties relative to the presence or absence of the active electrode within the plate condenser being detected. In addition, the condenser may also be designed as a coaxial condenser. In general, the recognized alteration of the dielectric properties of the condenser serves to derive the sensor signal, which in turn may be used to control the current supply unit.

Figure 1:
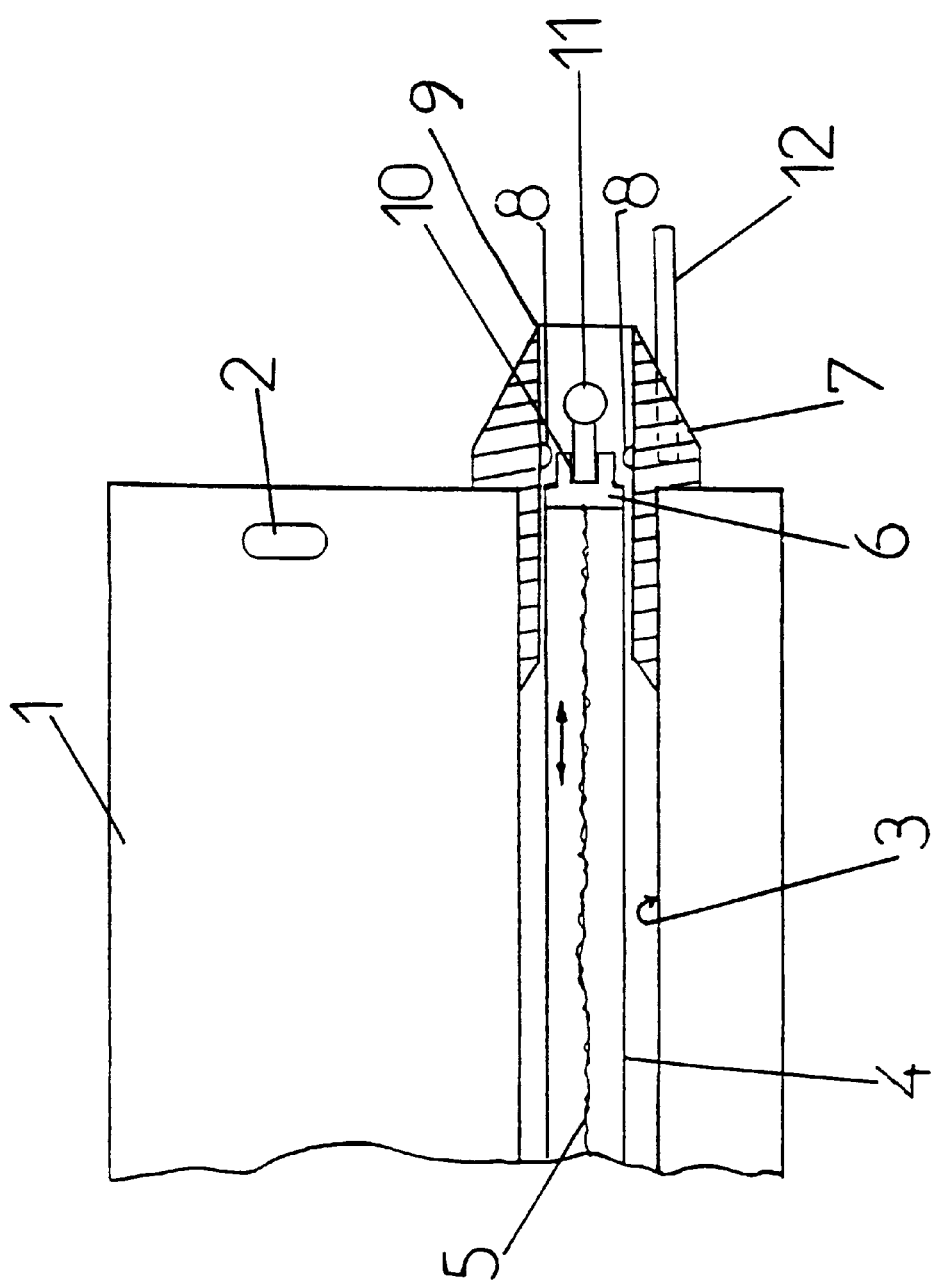
FIG. 1 is a cross-sectional view showing the endoscope, working channel, mobile applicator, current supply line, electrode, insert piece, sensor, and interchangeable spacer.

Preferably a flange-like insert piece with outlet opening for guiding the active electrode and for accommodating one of the above mentioned sensors is located at the distal end of the endoscope catheter. This insert piece consists of a temperature-resistant material, preferably ceramics. Properties of guiding the plasma beam or of diffusion can be ascribed in addition to the insert piece, these properties would be most applicable when the apparatus is in the non-contact mode. For example the argon-plasma coagulation is selected as a treatment method.

In a further development of the invention, it is possible to provide on the insert piece a replaceable spacer, which serves to predetermine or maintain a minimum spacing between outlet opening and the tissue to be coagulated.

Finally, the active electrode can comprise an interchangeable point, in order to satisfy corresponding requirements in contact mode or cutting, and to achieve the treatment results sought.

DETAILED DESCRIPTION OF THE PREFERRED EMBODIMENTS

FIG. 1 shows a theoretical cross-sectional view of the arrangement for HF-coagulation of biological tissues by means of flexible endoscopy.

An endoscope catheter 1 has an observation optical system 2 and at least one working channel 3. Located within the working channel is a mobile applicator 4, which has a handle at the proximal end (not shown). Ionizable gas is introduced at the proximal end of the applicator 4. The applicator 4 further comprises in its interior a current supply connection line 5, which is connected to a mobile active electrode 6.

The active electrode 6 can be moved relative to the distal end of the endoscope catheter 1 or the insert piece 7. For example, the electrode can move into the insert piece 7 for non-contact coagulation or out of it for contact coagulation.

The position of the active electrode 6 is monitored by means of a sensor 8.

In a simple case, the sensor 8 can be a micro-switch contact located in the range of the insert piece 7 such that when the active electrode 6 or the mobile applicator 4 is in the retracted position, it gives a signal which serves to release the parameters for argon-plasma coagulation. For example, a specific current-voltage range from a current supply unit not shown.

Alternatively it is possible for the sensor to be in the form of a miniature light barrier, which recognises the presence or otherwise of the active electrode upon interruption of the beam.

Likewise the sensor can comprise a plate or cylinder or coaxial condenser formed at the distal end of the applicator.

The preferably flange-like insert piece 7 formed at the distal end of the endoscope catheter 1 has an outlet opening 9, which affords the desired passage to the plasma beam.

Another embodiment would be to insert in the area of the outlet opening 9 a diffuser or a beam deflecting angle piece, in order to detect critical treatment spaces.

The free end of the active electrode 6 comprises means for accommodation 10, so that special electrode points, which again can have differing shapes, can be attached.

The interchangeable insert piece 7 consists of a temperature-resistant material, preferably ceramics. In conclusion there can be provided on the insert piece 7 an interchangeable spacer 12. This ensures minimum spacing between outlet opening and the tissue to be coagulated even under critical conditions of visibility.

In yet another embodiment it is possible to ensure that a coagulation current only flows when there is no risk of the occurrence of irreversible current injuries to the tissue by an advanced section of the active electrode. The arrangement envisaged can be combined with or supplemented by embodiments known per se of argon-plasma applicators and probes, the only point to be noted being that during alteration in position in the active electrode its respective position is used for a criterion of decision for the selection of current and voltage values in accordance with the respective treatment method.

List of Reference Numbers 1. endoscope catheter
2. observation optical system
3. working channel
4. mobile applicator
5. connecting line
6. active electrode
7. insert piece
8. sensor
9. outlet opening
10. accommodating means
11. point
12. spacer finger

I claim:

1. Apparatus for HF-coagulation of biological tissue comprising:
   an endoscope having a working channel;
   a mobile applicator insertable into the working channel for supplying ionizable gas to a distal end of said endoscope, said mobile applicator including a line for supplying current to the distal end of said endoscope;
   an electrode mounted to the mobile applicator and connected to the current supply line; and
   a sensor mounted near a distal end of said endoscope for detecting the electrode to verify a position of the electrode with respect to the endoscope prior to application of current to the supply line.

2. The apparatus of claim 1 including an insert piece mountable in the working channel to guide the mobile applicator.

3. The apparatus of claim 2 where said sensor is mounted in the insert piece.

4. The apparatus of claim 2 where said insert piece extends the working channel beyond the distal end of the endoscope.

5. The apparatus for claim 1 including an interchangeable electrode point mounted to said electrode.

6. The apparatus of claim 5 including a plurality of interchangeable electrode points.

7. The apparatus according to claim 1 where said electrode is movable relative to the distal end of the endoscope.

8. The apparatus according to claim 1 where said sensor is a switch contact.

9. The apparatus according to claim 1 where said sensor is a light barrier.

10. The apparatus according to claim 1 where said sensor comprises a plate, coaxial, or cylinder condenser.

11. The apparatus according to claim 1 where said sensor comprises a plate, coaxial, or cylinder condenser at the distal end of said applicator.

12. The apparatus according to claim 2 where said insert piece guides the electrode.

13. The apparatus according to claim 2 where said insert piece accommodates the sensor.

14. The apparatus according to claim 2 including an interchangeable spacer attachable to said insert piece.

15. The apparatus according to claim 2 where said insert piece comprises a temperature resistant material.

16. The apparatus according to claim 15 where said temperature resistant material is ceramic.

* * * * *